United States Patent [19]

Miyazaki et al.

[11] 4,384,133
[45] May 17, 1983

[54] PROCESS FOR THE PREPARATION OF OXALIC ACID DIESTERS

[75] Inventors: Haruhiko Miyazaki; Yasushi Shiomi, both of Ube; Satoru Fujitus, Yamaguchi; Katsuro Masunaga; Hiroshi Yanagisawa, both of Ube, all of Japan

[73] Assignee: UBE Industries, Ltd., Yamaguchi, Japan

[21] Appl. No.: 340,034

[22] Filed: Jan. 18, 1982

[30] Foreign Application Priority Data

Jan. 26, 1981 [JP] Japan .................................. 56-9035

[51] Int. Cl.³ ............................................. C07C 67/36
[52] U.S. Cl. ............................... 560/204; 252/429 C; 252/431 N; 252/431 P; 252/450; 252/458; 252/459; 252/470
[58] Field of Search .................... 560/204; 252/429 C, 252/431 N, 431 P, 450, 458, 459, 470

[56] References Cited

U.S. PATENT DOCUMENTS 4,138,587 2/1979 Yamasaki et al. .................. 560/204
4,229,589 10/1980 Nishimura et al. ................ 560/204
4,229,591 10/1980 Nishimura et al. ................ 560/204

*Primary Examiner*—Glennon H. Hollrah
*Assistant Examiner*—Vera C. Clarke
*Attorney, Agent, or Firm*—Sherman & Shalloway

[57] ABSTRACT

In a process for preparing a diester of oxalic acid by the vapor phase catalytic reaction of carbon monoxide with an ester of nitrous acid in the presence of a catalyst composed of a solid carrier and a catalyst component supported on the carrier, the improvement wherein said catalyst component is composed of (a) a platinum-group metal or a salt thereof, and
(b) at least one metal selected from the group consisting of Mo and Ni, or a salt thereof.

7 Claims, No Drawings

PROCESS FOR THE PREPARATION OF OXALIC ACID DIESTERS

This invention relates to an improved process for preparing a diester of oxalic acid by the vapor (or gaseous) phase catalytic reaction of carbon monoxide with an ester of nitrous acid in the presence of a catalyst composed of a solid carrier and a catalyst component supported on the carrier. According to this process, the diester of oxalic acid can be produced at a higher selectivity with a longer catalyst life than a conventional process involving using a platinum-group metal or a salt thereof alone as the catalyst component while maintaining an excellent space time yield.

More specifically, this invention relates, in the aforesaid vapor phase catalytic reaction, to the improvement which comprises using a catalyst composed of a solid carrier and a catalyst component supported on the carrier, said component being composed of (a) a platinum-group metal or a salt thereof and (b) at least one metal selected from Mo and Ni, or a salt thereof.

The process for preparing a diester of oxalic acid by the vapor phase catalytic reaction of carbon monoxide with an ester of nitrous acid in the presence of a catalyst composed of a solid carrier and metallic palladium or a salt thereof supported on the carrier is known (U.S. Pat. No. 4,229,591). This U.S. Patent, however, does not at all refer to the use of a co-catalyst component or a catalyst having such a second catalyst component supported together.

Japanese Laid-Open Patent Publication No. 22666/1980 (published on Feb. 18, 1980; corresponding UK patent application No. 2,025,950A) discloses another process for the production of a diester of oxalic acid by a similar vapor phase catalytic reaction to that shown in the above U.S. Patent. The Japanese patent document exemplified palladium, rhodium, iridium, platinum, gold and salts of these metals as ingredients of the catalyst, and iron, copper and salts of these as a carrier which concurrently serves as a catalyst promoter.

To the best of the knowledge of the present inventors, the prior literature including the two references cited above does not disclose the use of Mo, Ni or salt thereof as a catalyst component or catalyst promoter component for use in the vapor phase catalytic reaction of carbon monoxide with an ester of nitrous acid.

The present inventors have worked on the improvement of catalysts used in the aforesaid vapor phase catalytic reaction, and consequently found that by using a catalyst component supported on a solid carrier and composed of the aforesaid components (a) and (b), a diester of oxalic acid can be produced at a higher selectivity with a longer catalyst life than in the case of using a conventional catalyst comprising the component (a) on a solid carrier but not containing the component (b), while maintaining an excellent space time yield.

The work of the present inventors has shown that the use of the aforesaid catalyst composed of the components (a) and (b) supported concurrently on a solid carrier is advantageous over the conventional catalyst not containing the component (b) and that (i) the diester of oxalic acid can be produced at a higher selectivity while the space time yield of the oxalate in the initial stage of the reaction remains almost unchanged, and (ii) in a long-term reaction, the decrease of the space time yield of the oxalate is very small, and the oxalate can be produced stably over a long period of time.

It has also been found that the aforesaid catalyst is preferably formed by impregnating a solid carrier with an aqueous solution of a water-soluble salt of a platinum-group metal and an aqueous solution of a water-soluble salt of at least one metal selected from Mo and Ni, treating the impregnated solid carrier with an alkali, and then treating the alkali-treated product with a reducing agent in the liquid or gaseous phase; and that alternatively, the above procedure may be carried out by first impregnating the solid carrier with the aqueous solution of a water-soluble salt of a platinum-group metal, treating the impregnated solid carrier with an alkali, dipping the alkali-treated product in the aqueous solution of a water-soluble salt of Mo and/or Ni, and then treating the resulting product with a reducing agent in the liquid or gaseous phase.

It is an object of this invention therefore to provide an improved process for producing a diester of oxalic acid by vapor phase catalytic reaction using a specified catalyst.

The above and other objects of this invention along with its advantages will become more apparent from the following description.

Examples of the platinum-group metal used as the catalyst component (a) in this invention are palladium, platinum, rhodium, ruthenium and iridium. They may be used as a mixture of two or more. Palladium, either alone or in combination with another platinum-group metal, is preferred. Examples of the salt of the platinum-group metal include nitrates, sulfates, phosphates, halides, acetates, oxalates and benzoates of the above-exemplified metals.

Metallic molybdenum or nickel, or a salt thereof can be used as the catalyst component (b) in this invention. Examples of the salt are nitrates, halides and sulfates of Mo or Ni.

The ratio of the component (a) to the component (b) may be properly selected. Preferably, the atomic ratio of the component (a) to the component (b), as metal, is from 500:1 to 1:10, preferably from 100:1 to 1:5. If the amount of the component (b) is too small as compared with the component (a), the effect of the catalyst to inhibit formation of by-products (a carbonic acid diester and carbon dioxide) is reduced. If it is too large, the space time yield of the diester of oxalic acid is decreased. Accordingly, the ratio within the above-exemplified range is advantageously used.

The amount of the component (a) supported on the solid carrier is preferably 0.01 to 10% by weight, more preferably 0.1 to 2% by weight, as metal based on the weight of the solid carrier.

In this invention, both the components (a) and (b) are supported on the solid carrier. Examples of the carrier used include activated carbon, alumina, silica, diatomaceous earth, silicon carbide, pumice, zeolite and molecular sieves.

There is no restriction on the manner of supporting the catalytic metal components on the solid carrier, and any known means of supporting can be used. Preferably, however, the catalyst is prepared by impregnating a solid carrier with an aqueous solution of a water-soluble salt of a platinum-group metal and an aqueous solution of a water-soluble salt of at least one metal selected from Mo and Ni, treating the impregnated solid carrier with an alkali, and then treating the alkali-treated product with a reducing agent in the liquid or gaseous phase.

Alternatively, the above procedure is carried out by first impregnating the solid carrier with the aqueous solution of a water-soluble salt of a platinum-group metal, treating the impregnated solid carrier with an alkali, dipping the alkali-treated product in the aqueous solution of a water-soluble salt of Mo and/or Ni, and then treating the resulting product with a reducing agent in the liquid or gaseous phase.

Examples of the water-soluble salt of the platinum-group metal are nitrates, sulfates, acetates, phosphates, chlorides, chloro complex salts, and ammine complex salts of the above-exemplified platinum-group metals. Examples of the water-soluble salt of Mo are orthomolybdates, metamolybdates, and paramolybdates. Examples of the water-soluble salt of Ni are the nitrate, sulfate, acetate, phosphate, chloride and ammine complex salt.

The impregnation may be effected by dipping the solid carrier in an aqueous solution containing the water-soluble salt of the platinum-group metal and the water-soluble salt of Mo and/or Ni, or by dipping the solid carrier in a desired sequence in aqueous solutions of the respective water-soluble salts. As stated above, it is also possible to dip the solid carrier in the aqueous solution containing the water-soluble salt of the platinum-group metal, treat the impregnated solid carrier with an alkali, and then to dip the impregnated carrier in the aqueous solution of the water-soluble salt of Mo and/or Ni. The dipping may be performed at a temperature of, for example, about 0° C. to about 90° C. and a period of, for example, about 0.1 to about 10 hours. If desired, the impregnation may also be carried out by spraying the aforesaid aqueous solution onto the solid carrier.

Preferably, the above aqueous solutions are solutions prepared by dissolving the above water-soluble salts in an acidic aqueous solution containing about 0.01 to about 10% by weight of an acidic compound. The use of the acidic aqueous solution serves to aid in the dissolving of the platinum-group metal and to prevent the formation and precipitation of a hydroxide and oxide of the platinum-group metal by hydrolysis. Specific examples of the acidic compound include mineral acids such as hydrochloric acid, nitric acid, sulfuric acid and phosphoric acid and organic acids such as acetic acid. These acidic compounds may, if desired, be used as a mixture of two or more.

The carrier impregnated with the aqueous solutions containing the water-soluble salts is then separated, and if desired washed with water and then dried by, for example, air drying, vacuum drying or heat drying, after which it is subjected to the alkali treatment.

The alkali treatment can be effected by adding the carrier impregnated with the aqueous solutions of the above water-soluble salts to an alkaline aqueous solution containing about 0.5 to about 10% by weight of an alkaline compound, and stirring the mixture at a temperature of, for example, about 10° to about 90° C. for a period of, for example, about 0.5 to about 10 hours. Examples of the alkaline compound include the hydroxides and salts of alkali metals or alkaline earth metals, for example sodium hydroxide, potassium hydroxide, calcium hydroxide, barium hydroxide, sodium carbonate, sodium hydrogen carbonate and potassium carbonate. If desired, these alkaline compounds may be used as a mixture of two or more. There is no special limitation on the amount of the alkaline compound used. Preferably, it is about 2 to about 40 moles per mole of the sum of the platinum-group metal salt and the Mo and/or Ni salt.

After the alkali treatment, the product is optionally washed with water, etc. and dried. The product is then treated with a reducing agent in the liquid or gaseous phase to form the final catalyst.

The liquid-phase reduction is carried out by using such reducing agents as hydrazine, formaldehyde, sodium formate and formic acid. Specifically, it can be carried out by adding the alkali-treated product to an aqueous solution of the reducing agent in a concentration of about 0.5 to about 10% by weight, and stirring the mixture at a temperature of, say, about 10° to about 50° C. for a period of, say, about 0.5 to about 10 hours.

The alkaline-treated product may be added directly to the aqueous solution of the reducing agent in performing the reduction. It is more effective, however, to separate the alkali-treated solid product by a solid-liquid separating procedure such as filtration or decantation, wash and dry it, then add the dried product to the aqueous solution of the reducing agent, and subject the dried product to the reducing treatment in the liquid phase.

Examples of reducing agents suitable for use in the gaseous phase reduction are hydrogen, carbon monoxide and ammonia. These reducing agents may be used after being diluted with inert gases such as nitrogen or carbon dioxide. The gaseous phase reduction can be carried out by passing the gaseous reducing agent through the alkali-treated product at a temperature of, for example, about 100° to about 500° C. for a period of, say, about 0.5 to about 10 hours.

According to the process of this invention, carbon monoxide is reacted with an ester of nitrous acid in the vapor phase in the presence of the catalyst prepared as above which is composed of a solid carrier and a catalyst component supported on it, said component being composed of (a) a platinum-group metal or a salt thereof and (b) at least one metal selected from Mo and Ni or a salt thereof. This reaction can be schematically shown by the following equation.

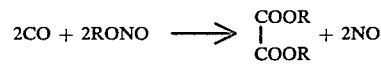

(R=alkyl or cycloalkyl)

As the above scheme shows, this reaction yields nitrogen monoxide equivalent to the consumed nitrous acid ester. Accordingly, the nitrogen monoxide thus formed may be recycled as the starting material for the above reaction by introducing an alcohol and a gas containing molecular oxygen to react them with the nitrogen monoxide as schematically shown below and recovering the resulting nitrous acid ester.

(R=alkyl or cycloalkyl)

An ester of nitrous acid with a saturated monohydric aliphatic alcohol having 1 to 8 carbon atoms or an alicyclic alcohol having 1 to 8 carbon atoms is preferred as the ester of nitrous acid. Examples of the aliphatic alcohol are methanol, ethanol, n-propanol, isopropanol, n-butanol, isobutanol, sec-butanol, tert-butanol, n-amyl alcohol, isoamyl alcohol, hexanol and octanol, and examples of the alicyclic alcohol include cyclohexanol, and methylcyclohexanol. These alcohols may contain a substituent, such as an alkoxy group, which does not inhibit the reaction.

The concentration of the ester of nitrous acid used may be varied over a wide range. To obtain a satisfactory rate of reaction, it is desirable to adjust the concentration of the nitrous acid ester in the starting gaseous mixture introduced into the reactor at 1% by volume or higher, for example about 5 to about 30% by volume.

Carbon monoxide used in the process of this invention may be pure or may be diluted with an inert gas such as nitrogen. The concentration of carbon monoxide in the reaction zone may be varied over a wide range and is usually in the range of 10 to 90% by volume.

The reaction is carried out under such conditions that no liquid phase is formed in the reaction zone (namely, in the gaseous or vapor phase). These conditions may vary depending upon the reaction temperature, the reaction pressure, the type and concentration of the nitrous acid ester, etc. Thus, these conditions may be properly selected so that the reaction is carried out in the vapor phase.

The reaction proceeds rapidly even at low temperatures, and side-reactions occur less as the reaction temperature is lower. Hence, it is desirable to perform the reaction at a relatively low temperature at which the desired space time yield can be maintained, for example at a temperature of about 50° C. to about 200° C., preferably at about 80° C. to about 150° C. The reaction pressure can also be selected properly. For example, it is atmospheric pressure to about 10 $kg/cm^2$.G, preferably atmospheric pressure to about 5 $kg/cm^2$.G. Pressures below the above-specified lower limit, for example reduced pressures of down to about 200 mmHg, can also be used.

The catalytic reaction in accordance with this invention may be carried out in a fixed or fluidized bed. The time of contact between the starting gaseous mixture and the catalyst can be properly chosen. For example, the contact time is not more than about 20 seconds, preferably about 0.2 to about 10 seconds.

The nitrous acid ester can be prepared, for example, by reacting an alcohol with a nitrogen oxide in the optional presence of molecular oxygen. The reaction product gas contains the unreacted alcohol and nitrogen oxide (particularly nitrogen monoxide) and at times, traces of water and oxygen in addition to the desired nitrous acid ester. In the process of this invention, this product gas containing the nitrous acid ester can be used as the starting nitrous acid ester, and good results can be obtained even when such a nitrite containing impurities is used.

The following examples illustrate the practice of the process of the invention in greater detail.

CATALYST PREPARATION EXAMPLE 1

Palladium chloride (1.46 parts by weight) was dissolved in 68.4 parts by weight of a 0.9% by weight aqueous solution of hydrochloric acid. Spherical gamma-alumina particles having a diameter of 3 mm (50 parts by weight) were dipped in the solution, and the solution was stirred at room temperature for 2 hours to impregnate palladium chloride.

The alumina impregnated with palladium chloride was separated by decantation, dried, and then dipped in 70 parts by weight of a 2% by weight aqueous solution of sodium hydroxide to treat it with the alkali at 60° C. for 4 hours with stirring. The alkali-treated product was washed with water until a chlorine ion was no longer detected in the washing. The washed alkali-treated product was dried, and dipped for 1 hour in 70 parts by weight of a 2.1% by weight aqueous solution of ammonium molybdate. The treated product was separated by decantation from the mother liquor, dried.

The dried product was then dipped in an aqueous hydrazine solution consisting of 3 parts by weight of 85% hydrazine hydrate and 97 parts by weight of water, and the solution was stirred at room temperature for about 4 hours to reduce.

The reduction product was decanted, washed with water and dried to give a spherical supported catalyst having a particle diameter of 3 mm and composed of gamma-alumina and 0.5% by weight of palladium and 0.45% by weight of molybdenum supported on it.

CATALYST PREPARATION EXAMPLE 2

Palladium chloride (1.46 parts by weight) and 3.52 parts by weight of nickel chloride hexahydrate were dissolved in 68.4 parts by weight of a 0.9% by weight aqueous solution of hydrochloric acid. Spherical gamma-alumina particles having a diameter of 3 mm (50 parts by weight) were dipped in the solution, and the solution was stirred at room temperature for 2 hours.

The alumina impregnated with palladium chloride and nickel chloride was separated by decantation, and dried. The dried alumina was then dipped in a solution of 1.5 parts by weight of sodium hydroxide in 68.5 parts by weight of water to treat it with the alkali at about 60° C. for 4 hours.

The alkali-treated product was washed with water until the washing became neutral and a chlorine ion was no longer detected.

The dried product was then dipped in an aqueous hydrazine solution consisting of 3 parts by weight of 85% hydrazine hydrate and 97 parts by weight of water, and the solution was stirred at room temperature for about 4 hours to reduce.

The reduction product was decanted, washed with water and dried to give a spherical supported catalyst having a particle diameter of 3 mm and composed of gamma-alumina and 0.5% by weight of palladium and 0.5% by weight of nickel supported on it.

CATALYST PREPARATION EXAMPLE 3

Palladium chloride (1.46 parts by weight) was dissolved in 68.4 parts by weight of a 0.9% by weight aqueous solution of hydrochloric acid. Spherical alpha-alumina particles having a diameter of 3 mm (50 parts by weight) were dipped in the solution, and the solution was stirred at room temperature for 2 hours to impregnate palladium chloride.

The alumina impregnated with palladium chloride was separated by decantation, dried, and then dipped in 70 parts by weight of a 2% by weight aqueous solution of sodium hydroxide to treat it with the alkali at 60° C. for 4 hours with stirring. The alkali-treated product was washed with water until a chlorine ion was no longer detected in the washing. The washed alkali-treated product was dried, and dipped for 1 hour in 70 parts by weight of a 0.21% by weight aqueous solution of ammonium molybdate. The treated product was separated by decantation from the mother liquor, dried, and then subjected to reducing treatment in a hydrogen stream at 500° C. for 3 hours.

There was obtained a catalyst composed of alpha-alumina having a diameter of 3 mm and 0.5% by weight of Pd and 0.045% by weight of Mo supported on it.

CATALYST PREPARATION EXAMPLE 4

Palladium chloride (1.46 parts by weight) and 0.197 part by weight of nickel chloride hexahydrate were dissolved in 68.4 parts by weight of a 0.9% by weight aqueous solution of hydrochloric acid. Spherical alpha-alumina particles having a diameter of 3 mm (50 parts by weight) were dipped in the solution, and the solution was stirred at room temperature for 2 hours.

The alumina impregnated with palladium chloride and nickel chloride was separated by decantation, and dried. The dried alumina was then dipped in a solution of 1.5 parts by weight of sodium hydroxide in 68.5 parts by weight of water to treat it with the alkali at about 60° C. for 4 hours.

The alkali-treated product was washed with water until the washing became neutral and a chlorine ion was no longer detected. It was then dried and subjected to reducing treatment in a hydrogen stream at 500° C. for 3 hours.

There was obtained a catalyst composed of alpha-alumina having a diameter of 3 mm and 0.5% by weight of Pd and 0.028% by weight of Ni supported on it.

EXAMPLE 1

Ten milliliters of a catalyst composed of gamma-alumina and 0.5% by weight of palladium and 0.45% by weight of molybdenum supported on it, prepared in Catalyst Preparation Example 1, was filled in a glass reaction tube having an inside diameter of 20 mm and a length of 55 cm. Then, glass beads were further filled in the reaction tube and placed on the catalyst layer to a height of 20 cm.

The reaction tube was fixed vertically, and an annular electric heater was mounted on the outside of the reaction tube to maintain the temperature of the catalyst layer at 110° C.

From the top of the reaction tube, a gaseous mixture consisting of 20% by volume of carbon monoxide, 15% by volume of methyl nitrite, 15% by volume of methanol, 3% by volume of nitrogen monoxide and 47% by volume of nitrogen was fed into the reactor at a space velocity of 2,000 hr$^{-1}$, and reacted under atmospheric pressure.

The reaction product which left the reaction tube was passed through methanol to collect dimethyl oxalate. Low-boiling compounds not collected by methanol were then condensed by cooling with dry ice/methanol and collected. The liquids collected were each analyzed by gas chromatography. The results are shown in Table 1.

EXAMPLE 2

The procedure of Example 1 was followed except that 10 ml of a catalyst composed of gamma-alumina and 0.5% by weight of palladium and 0.5% by weight of nickel supported on it, prepared in Catalyst Preparation Example 2, was used as the catalyst. The results are shown in Table 1.

COMPARATIVE EXAMPLE 1

A catalyst was prepared in the same way as in Catalyst Preparation Example 1 except that after the alkali-treated product was washed and dried, it was subjected to the reducing treatment without impregnation of the molybdenum compound.

The procedure of Example 1 was followed except that 10 ml of the resulting catalyst composed of gamma-alumina and 0.5% by weight of palladium supported on it was used as the catalyst. The results are shown in Table 1.

TABLE 1

| | Selectivity (%) based on methyl nitrite | | |
|---|---|---|---|
| | Dimethyl oxalate (*1) | Dimethyl carbonate | Others (*2) |
| Example 1 | 94.57 | 4.46 | 0.97 |
| Example 2 | 94.95 | 3.84 | 1.21 |
| Comparative Example 1 | 88.40 | 9.10 | 2.50 |

(*1): The space time yield of dimethyl oxalate was about 400 g/liter · hr in all of these examples.
(*2): Methyl formate and methylal were the main products.

EXAMPLE 3

The procedure of Example 1 was followed except that a gaseous mixture composed of 20% by volume of carbon monoxide, 15% by volume of methyl nitrite and 65% by volume of nitrogen was fed at a space velocity of 2,000 hr$^{-1}$ as the starting gas. There were obtained dimethyl oxalate, dimethyl carbonate, methyl formate and methylal in a selectivity, based on methyl nitrite, of 93.37, 4.78, 1.74, and 0.11%, respectively.

EXAMPLE 4

Ten milliliters of the same catalyst as used in Example 1 was filled in a jacketed glass reaction tube having an inside diameter of 20 mm and a length of 55 cm, and glass beads were further introduced into the reaction tube and placed on the catalyst layer to a height of 20 cm. The reaction tube was fixed vertically, and a heat transfer medium was circulated through the jacket to maintain the temperature of the catalyst layer at 120° C.

From the top of the reaction tube, a gaseous mixture consisting of 60% by volume of carbon monoxide, 8% by volume of ethyl nitrite and 32% by volume of nitrogen was fed at a space velocity of 3,900 hr$^{-1}$ into the reaction tube, and reacted under atmospheric pressure.

The reaction product which left the reaction tube was passed through a condenser through which ice water was circulating, and collected by cooling. The product was analyzed by gas chromatography, and found to contain 37.67 mmoles/hr (space time yield 550 g/liter.hr) of diethyl oxalate in a selectivity of 90.5% based on ethyl nitrite.

EXAMPLE 5

The procedure of Example 1 was followed except that 10 ml of a catalyst composed of gamma-alumina and 0.5% by weight of palladium and 0.023% by weight of molybdenum supported on it, prepared as in Catalyst Preparation Example 1, was used as the catalyst. Dimethyl oxalate and dimethyl carbonate were obtained in a selectivity, based on methyl nitrite, of 93.35% and 5.56%, respectively. The amounts of methyl formate and methylal formed were small.

EXAMPLE 6

The procedure of Example 1 was followed except that 10 ml of a catalyst composed of gamma-alumina and 0.5% by weight of palladium and 0.01% by weight of nickel supported on it, prepared as in Catalyst Preparation Example 2 was used as the catalyst. Dimethyl oxalate and dimethyl carbonate were formed in a selectivity, based on methyl nitrite, of 92.74% and 6.18%, respectively. The amounts of methyl formate and methylal formed were small.

EXAMPLE 7

Ten milliliters of the same catalyst as used in Example 2 was filled in a stainless steel reaction tube having an inside diameter of 23 mm and a length of 55 cm, and glass beads were further introduced into the reaction tube and placed on the catalyst layer to a height of 20 cm. The reaction tube was fixed vertically, and an annular electric heater was mounted on the outside of the reaction tube to maintain the temperature of the catalyst layer at 110° C.

From the top of the reaction tube, a gaseous mixture consisting of 20% by volume of carbon monoxide, 15% by volume of methyl nitrite, 3% by volume of nitrogen monoxide, 4% by volume of methanol and 58% by volume of nitrogen was fed into the reaction tube at a rate of 18.6 Nl/hr, and reacted under a pressure of 2.0 kg/cm$^2$.G.

The reaction product which left the reaction tube was passed through methanol to collect dimethyl oxalate. Low-boiling compounds not collected by methanol were then condensed by cooling with dry ice/methanol and collected. The liquids collected were each analyzed by gas chromatography.

Dimethyl oxalate was obtained in a space time yield of 332 g/liter.hr, and the selectivities of dimethyl oxalate and dimethyl carbonate, based on methyl nitrite, were 94.45% and 4.45%, respectively.

EXAMPLE 8

The procedure of Example 7 was followed except that 10 ml of the same supported catalyst as used in Example 2 was used, and a gaseous mixture composed of 20% by volume of carbon monoxide, 9.2% by volume of methyl nitrite, 3% by volume of nitrogen monoxide, 2% by volume of methanol and 65.8% by volume of nitrogen was fed into the reaction tube from its top at a rate of 38.7 Nl/hr, and reacted under a pressure of 4.6 kg/cm$^2$.G.

Dimethyl oxalate was obtained in a space time yield of 316 g/liter.hr. The selectivities, based on methyl nitrite, of dimethyl oxalate and dimethyl carbonate were 95.0% and 3.8%, respectively.

EXAMPLE 9

Two milliliters of a catalyst composed of spherical alpha-alumina (3 mm in diameter) and 0.5% by weight of palladium and 0.045% by weight of molybdenum supported on it, prepared in Catalyst Preparation Example 3, was filled in a jacketed glass reaction tube having an inside diameter of 20 mm and a length of 55 cm, and glass beads were further filled into the reaction tube and placed on the catalyst layer to a height of 24 cm. The reaction tube was fixed vertically, and a heat transfer medium was circulated through the jacket to maintain the temperature of the catalyst layer at 110° C.

From the top of the reaction tube, a gaseous mixture consisting of 20% by volume of carbon monoxide, 15% by volume of methyl nitrite, 3% by volume of nitrogen monoxide, 15% by volume of methanol and 47% by volume of nitrogen was fed into the reaction tube at a rate of 20 liters/hr (in a normal temperature-pressure condition), and reacted. The reaction product which left the reaction tube was first passed through methanol to collect dimethyl oxalate. The remainder was passed through a dry ice/methanol trap to collect low-boiling compounds by cooling. The liquids collected were each analyzed by gas chromatography 8 hours after the start of the reaction and after the lapse of each of the times indicated in Table 2. The space time yield (g/liter.hr) of dimethyl oxalate at these times was measured. The results are shown in Table 2.

EXAMPLES 10 and 11

The procedure of Example 9 was followed except that the reaction temperature was changed to 130° C. (Example 10), and 150° C. (Example 11). The results are shown in Table 2.

EXAMPLE 12

The procedure of Example 9 wss followed except that 2 ml of a catalyst composed of spherical alpha-alumina (3 mm in diameter) and 0.5% by weight of palladium and 0.028% by weight of nickel supported on it, prepared in Catalyst Preparation Example 4, was used as the catalyst. The results are shown in Table 2.

EXAMPLE 13

The procedure of Example 12 was followed except that the reaction temperature was changed to 130° C. The results are shown in Table 2.

COMPARATIVE EXAMPLE 2

A catalyst composed of spherical alpha-alumina (3 mm in diameter) and 0.5% by weight of palladium supported on it was prepared in the same way as in Catalyst Preparation Example 3 except that the impregnation of ammonium molybdate was omitted. The procedure of Example 9 was followed except that the resulting catalyst was used. The results are shown in Table 2.

COMPARATIVE EXAMPLE 3

The procedure of Example 10 was followed except that a catalyst composed of spherical alpha-alumina (3 mm in diameter) and 0.55% by weight of palladium prepared as in Comparative Example 2 was used as the catalyst. The results are shown in Table 2.

COMPARATIVE EXAMPLE 4

The procedure of Example 11 was followed except that a catalyst composed of spherical alpha-alumina (3 mm in diameter) and 0.55% by weight of palladium supported on it, prepared as in Comparative Example 2, was used as the catalyst. The results are shown in Table 2.

In Table 2 below, the percent decreases of the space time yields of dimethyl oxalate are based on the space time yield measured 8 hours after the start of the reaction, and calculated in accordance with the following equation.

TABLE 2

$$\text{Percent decrease of the space time yield of dimethyl oxalate (\%)} = \left(1 - \frac{\text{Space time yield of dimethyl oxalate at each reaction time elapsed}}{\text{Space time yield of dimethyl oxalate at 8 hours after the start of the reaction}}\right) \times 100$$

| | | Catalyst components supported (wt. %) | | Reaction temperature (°C.) | Reaction time elapsed (hours) | Percent decrease of the space time yield of dimethyl oxalate (%) |
|---|---|---|---|---|---|---|
| | | Pd | Mo or Ni | | | |
| Example | 9 | 0.5 | Mo 0.045 | 110 | 366 | 8.3 |
| | | | | | 534 | 11.2 |
| | 10 | 0.5 | 0.045 | 130 | 220 | 8.1 |
| | | | | | 550 | 14.6 |
| | 11 | 0.5 | 0.045 | 150 | 344 | 8.9 |
| | | | | | 600 | 9.5 |
| | 12 | 0.5 | Ni 0.028 | 110 | 222 | 9.0 |
| | | | | | 534 | 18.7 |
| | 13 | 0.5 | 0.028 | 130 | 336 | 7.9 |
| | | | | | 600 | 11.7 |
| Comparative Example | 2 | 0.5 | 0 | 110 | 342 | 11.7 |
| | | | | | 670 | 33.4 |
| | 3 | 0.55 | 0 | 130 | 199 | 32.6 |
| | | | | | 367 | 63.2 |
| | 4 | 0.55 | 0 | 150 | 264 | 11.9 |
| | | | | | 575 | 27.5 |

What we claim is:

1. In a process for preparing a diester of oxalic acid by the vapor phase catalytic reaction of carbon monoxide with an ester of nitrous acid in the presence of a catalyst composed of a solid carrier and a catalyst component supported on the carrier, the improvement wherein said catalyst component is composed of (a) a platinum-group metal or a salt thereof, and (b) at least one metal selected from the group consisting of Mo and Ni, or a salt thereof wherein the atomic ratio of the component (a) to the component (b) as metal is from 500:1 to 1:10 and wherein the amount of the component (a) supported is about 0.01 to about 10% by weight calculated as the platinum-group metal based on the weight of the carrier.

2. The process of claim 1 wherein said ester of nitrous acid is an ester of nitrous acid with an alcohol having 1 to 8 carbon atoms selected from the group consisting of saturated monohydric aliphatic alcohols and alicyclic alcohols.

3. The process of claim 1 wherein the catalytic reaction is carried out at a temperature of about 50° C. to about 200° C.

4. The process of claim 1 wherein the catalytic reaction is carried out at a pressure ranging from atmospheric pressure to about 10 kg/cm² G.

5. The process of claim 1 wherein said catalyst is prepared by impregnating the solid carrier with an aqueous solution of a water-soluble salt of the platinum-group metal and an aqueous solution of a water-soluble salt of at least one metal selected from Mo and Ni, treating the impregnated solid carrier with an alkali, and then subjecting the alkali-treated product to reducing treatment in the liquid or gaseous phase.

6. The process of claim 1 wherein said catalyst is prepared by impregnating the solid carrier with an aqueous solution of a water-soluble salt of the platinum-group metal, treating the impregnated solid carrier with an alkali, dipping the alkali-treated product in an aqueous solution of a water-soluble salt of at least one metal selected from Mo and Ni, and then subjecting the resulting product to reducing treatment in the liquid or gaseous phase.

7. The process of claim 5 or 6 wherein said alkali is selected from the group consisting of hydroxides, carbonates and bicarbonates of alkali metals or alkaline earth metals.

* * * * *